(12) United States Patent
Rubino et al.

(10) Patent No.: US 11,083,538 B2
(45) Date of Patent: Aug. 10, 2021

(54) DENTAL INSTRUMENT WITH REMOVABLE DENTAL TIP AND METHOD OF ASSEMBLY

(71) Applicant: American Eagle Instruments, LLC, Missoula, MT (US)

(72) Inventors: Samuel Rubino, Boulder, CO (US); Patrick Schwab, Missoula, MT (US); Philippe Leiritz, Missoula, MT (US); Bobby Horowitz, Huson, MT (US)

(*) Notice: Subject to any disclaimer, the term of this patent is extended or adjusted under 35 U.S.C. 154(b) by 449 days.

(21) Appl. No.: 15/899,477

(22) Filed: Feb. 20, 2018

(65) Prior Publication Data

US 2018/0235727 A1 Aug. 23, 2018

Related U.S. Application Data

(60) Provisional application No. 62/460,367, filed on Feb. 17, 2017.

(51) Int. Cl.
| | | |
|---|---|---|
| *A61C 3/08* | (2006.01) | |
| *A61B 1/247* | (2006.01) | |
| *A61C 3/00* | (2006.01) | |
| *A61B 1/00* | (2006.01) | |

(52) U.S. Cl.
CPC ............ *A61C 3/08* (2013.01); *A61B 1/00101* (2013.01); *A61B 1/00105* (2013.01); *A61B 1/247* (2013.01); *A61C 3/00* (2013.01)

(58) Field of Classification Search
CPC ......... A61C 3/08; A61C 3/00; A61B 1/00101; A61B 1/00105; A61B 1/247
See application file for complete search history.

(56) References Cited

U.S. PATENT DOCUMENTS

| | | |
|---|---|---|
| 5,407,293 A | 4/1995 | Crainich |
| 6,045,564 A | 4/2000 | Walen |
| 6,322,362 B1 | 11/2001 | Holms |
| 2006/0057536 A1 | 3/2006 | Tamburrino et al. |

(Continued)

FOREIGN PATENT DOCUMENTS

EP    1669040 A1    6/2006

OTHER PUBLICATIONS

International Search Report and Written Opinion dated Jun. 1, 2018 in International (PCT) Application No. PCT/US2018/018668.

(Continued)

*Primary Examiner* — Heidi M Eide
*Assistant Examiner* — Drews Folgmann
(74) *Attorney, Agent, or Firm* — McDermott Will & Emery LLP

(57) ABSTRACT

A dental instrument includes at least one removable or replaceable dental tip. The dental instrument includes a spring actuated collet and collar housed internally within a handle. The handle includes a handle center affixed to a center rod and a grip portion housing the collet and collar and a handle center affixed to a center rod. The center rod is affixed to the collet. The collet includes spring fingers that are biased radially inward by the collar to retain the dental tip. When the grip portion of the handle is rotated about a longitudinal axis of the handle relative to the handle center, camming surfaces associated with the grip portion and the handle center cause translational movement along the longitudinal axis to engage or disengage the collar from the collet.

22 Claims, 21 Drawing Sheets

(56) References Cited

U.S. PATENT DOCUMENTS

2007/0003903 A1\* 1/2007 Meuchel ............... A61B 90/92
                                                   433/141
2007/0218423 A1   9/2007  Sapian
2015/0125816 A1   5/2015  Ladd et al.
2015/0313612 A1   11/2015 Edwards et al.

OTHER PUBLICATIONS

Extended European Search Report issued in European Application No. 18754650.2.

\* cited by examiner

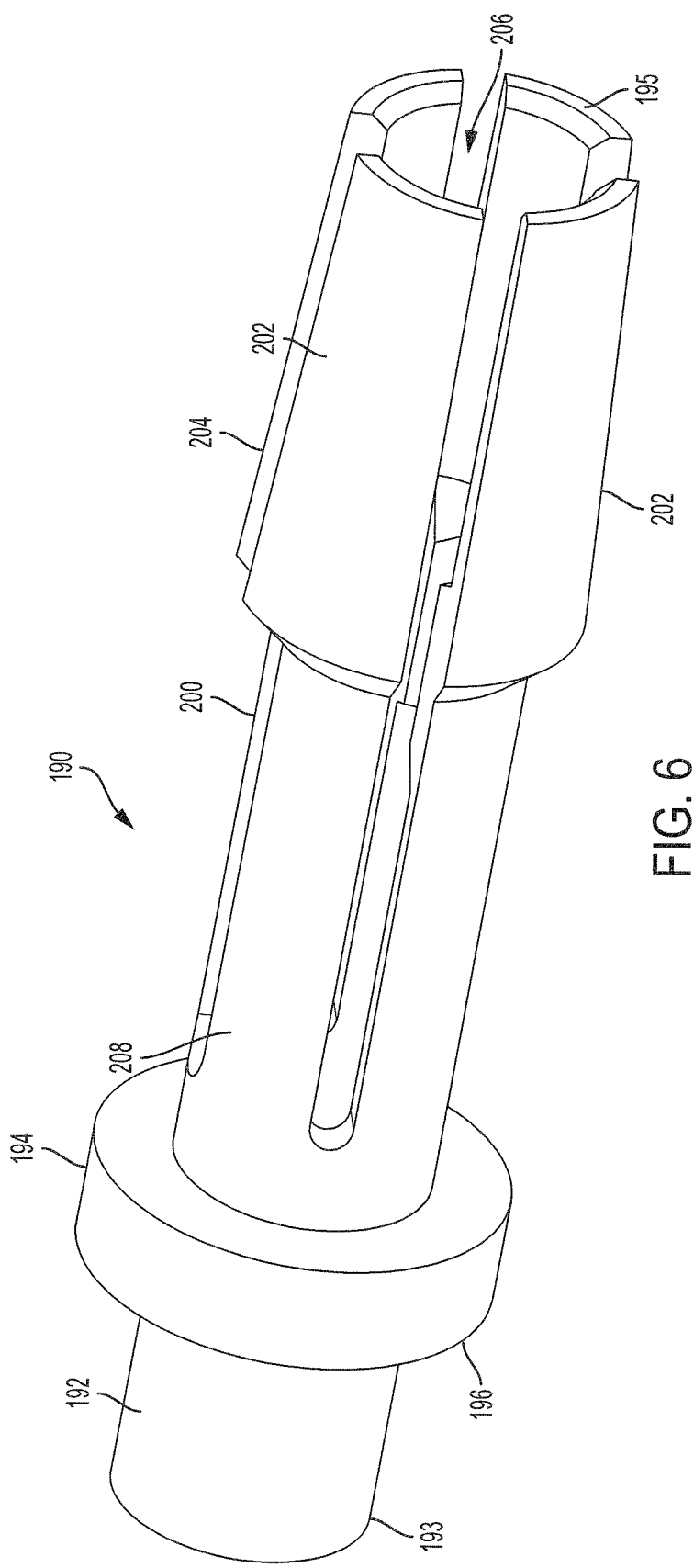

DENTAL INSTRUMENT WITH REMOVABLE DENTAL TIP AND METHOD OF ASSEMBLY

RELATED APPLICATIONS

The present application claims priority to, and the benefit of, U.S. Provisional Patent Application No. 62/460,367, titled "DENTAL INSTRUMENT WITH REMOVABLE DENTAL TIP AND METHOD OF ASSEMBLY" and filed on Feb. 17, 2017, the entire contents of which are hereby incorporated by reference for all purposes.

TECHNICAL FIELD

This invention relates generally to a dental instrument, and more particularly, to a dental instrument including at least one removable tip.

BACKGROUND OF THE INVENTION

Dental instruments are used by dentists and dental hygienists to clean, explore and repair teeth. Dental instruments typically include a dental tip that performs the necessary action by the dentist or dental hygienist. For example, scalers are used to scrape away tarter, while probes are used to examine the status of the teeth. Over time, dental tips become worn out or broken, or must be sharpened.

SUMMARY OF THE INVENTION

The shortcomings of the prior art may be alleviated by using a dental instrument constructed in accordance with one or more principles of the present invention. The dental instrument may use a variety of dental tips, such as, for example, scaler, a scraper, mouth mirror, reamer, file, chisel, probe, excavator, hollenback, burnisher, scooper, curette, plugger, locator and buffer. Additionally, other dental tips may be used that fall within the scope of the claimed invention but which are not specifically described below.

In one aspect of the invention, there is provided a dental instrument comprising a dental tip, a handle, a collar, a collet and a center rod. The dental tip includes a first end and a second end. The handle includes a handle center and a grip portion. The handle also includes an axis and an elongated opening extending along the axis though the handle center and the grip portion. The handle center includes a first surface. The grip portion includes a dental tip entrance end and a second surface in engagement with the first surface of the handle center. The second surface of the grip portion is rotatable about the axis relative to the first surface of the handle center. Rotation of the second surface of the grip portion relative to the first surface of the handle center causes translation along the axis of the grip portion relative to the handle center between a first axial position and a second axial position. The collar is disposed within the elongated opening proximate the dental tip entrance end of the grip portion. The collar includes a bore extending along the axis between a first opening proximate to and aligned with the dental tip entrance end of the grip portion and a second opening. The collet includes a body portion and spring fingers extending from the body portion. The spring fingers include a dental tip retaining portion configured to receive the second end of the dental tip. The spring fingers are urged radially inward by the collar towards the axis to secure the second end of the dental tip when the grip portion is in the first axial position relative to the handle center. The second end of the dental tip is removable from the dental tip retaining portion of the spring fingers of the collet when the grip portion is in the second axial position relative to the handle center. The center rod extends along the axis. At least a portion of the center rod is affixed to the handle center. The center rod includes an end affixed to the body portion of the collet.

In another aspect of the invention, dental instrument may include a second dental tip, a second grip portion, a second collar and a second collet that are configured in the same manner on the opposite side of the handle center and operate independently from the removal and insertion of the dental tip on the other side of the handle center.

In another aspect of the invention, translation along the axis of the grip portion relative to the handle center between the first axial position and the second axial position results from contact of a first inclined surface of the handle center with a second inclined surface of the grip portion during rotation of the grip portion relative to the handle center.

In another aspect of the invention, translation along the axis of the grip portion relative to the handle center between the first axial position and the second axial position results from engagement of a cam path formed at or proximate an end of the handle center and a cam follower located proximate an end of the grip portion during rotation of the grip portion relative to the handle center. In another example, the cam path may be formed at or proximate an end of the grip portion and the cam follower may be located proximate an end of the handle center.

Additional features and benefits will become apparent from the following drawings and descriptions of the invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the end of the specification. The foregoing and other objects, features, and advantages of the invention are apparent from the following detailed description taken in conjunction with the accompanying drawings in which:

FIG. 6 depicts a perspective view of one embodiment of a collet constructed in accordance with one or more aspects of the present invention;

DETAILED DESCRIPTION

Figure 1A:
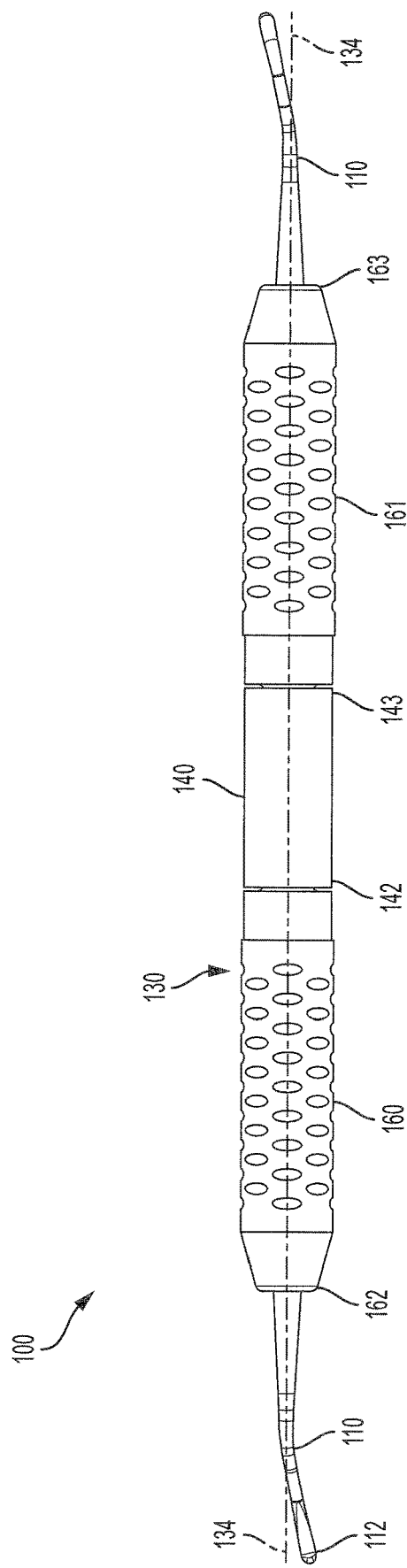
FIG. 1A depicts a side view of one embodiment of a dental instrument constructed in accordance with one or more aspects of the present invention.
Figure 1B:
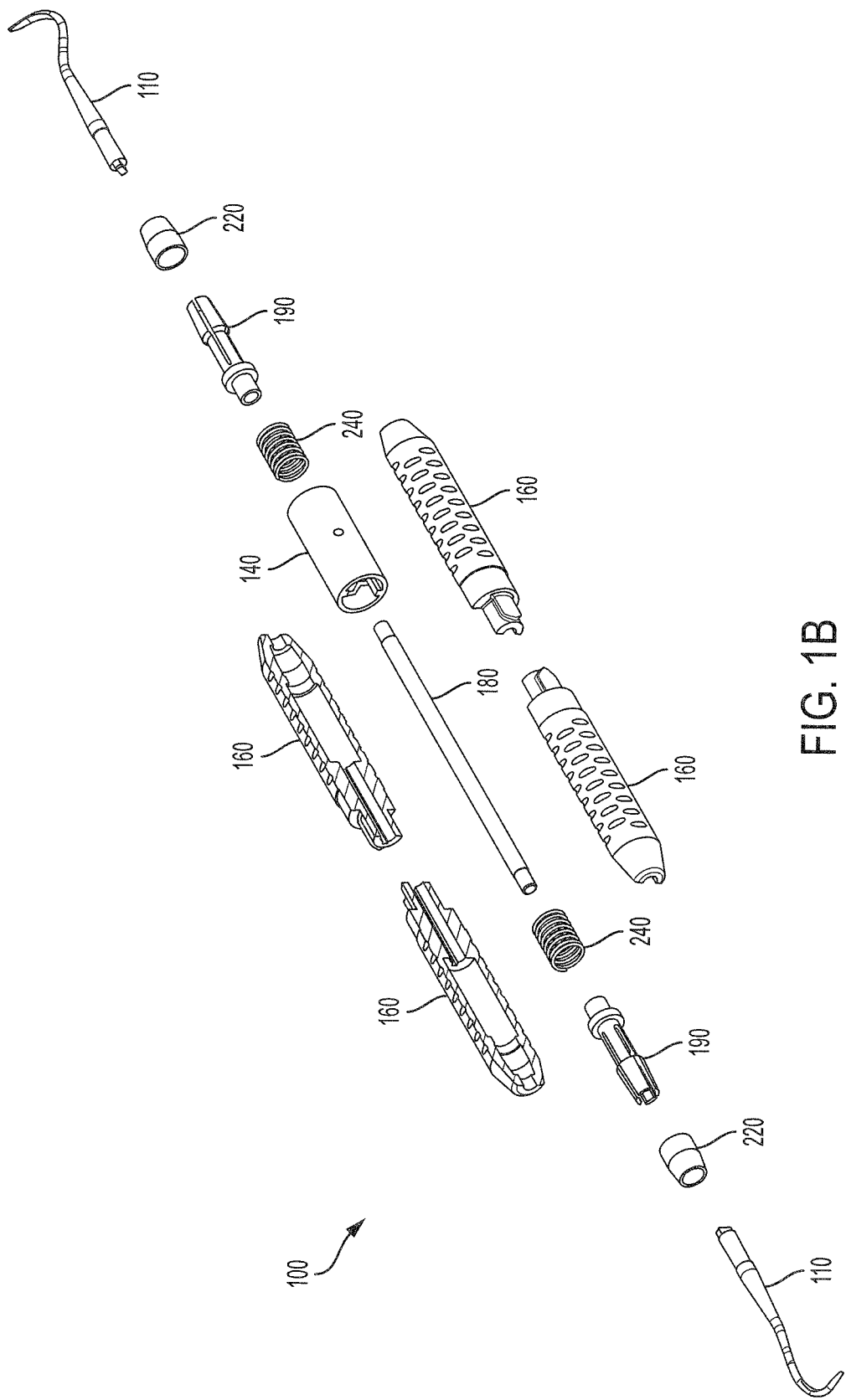
FIG. 1B depicts an exploded view of one embodiment of a dental instrument constructed in accordance with one or more aspects of the present invention.

For the purposes of promoting an understanding of the principles of a dental instrument designed and constructed in accordance with one or more aspects of the present invention, reference will now be made to the embodiments, or examples, illustrated in the drawings and specific language will be used to describe these. It will nevertheless be understood that no limitation of the scope of the invention is thereby intended. Any alterations and further modifications in the described embodiments, and any further applications of the principles or aspects of the invention as described herein are contemplated as would normally occur to one skilled in the art to which the dental instrument invention relates.

Presented herein is a dental instrument designed to provide dental hygiene professionals the capability to remove and/or replace dental tips. The dental instrument constructed in accordance with one or more aspects of the present invention does not require a supplementary tool to remove or replace the dental tips. Also, the dental instrument may be sterilized without removing the dental tips. The dental instrument may be single-ended to include a removable or replaceable dental tip only at one end, or, alternatively, double-ended to include a dental tip at both ends where both dental tips are removable or replaceable.

A dental instrument constructed in accordance with one or more aspects of the present invention is useful in the dental field to, for example, replace a worn out dental tip and replace a dental tip with another dental tip. By way of example only and without limitation, the dental tip used by a dental instrument constructed in accordance with one or more aspects of the present invention may be designed to perform a wide variety of tasks common to the dental industry, such as, for example, a scaler, scraper, mouth mirror, reamer, file, chisel, probe, excavator, hollenback, burnisher, scooper, plugger, locator and buffer.

In one example, the dental tips may be retained by a spring-actuated collet and a collar housed internally within the handle of the dental instrument. When a grip portion of the handle is rotated relative to a handle center, camming surfaces on opposing surfaces of the grip portion and the handle center cause the collar to disengage from a tapered portion of the collet to allow the dental tip to be removed or inserted. Rotation of the grip portion in reverse, for example, causes the collar to re-engage the collet and retain the dental tip within the handle.

FIGS. 1A, 1B, 2A and 2B illustrate one example of a dental instrument 100 constructed in accordance with one or more aspects of the present invention. As depicted in FIG. 1A, dental instrument 100 includes two dental tips 110 and a handle 130. Handle 130 includes a handle center 140 and two grip portions 160, 161 located at opposing ends 142, 143 of handle center 140. In one example illustrated in FIG. 1B, grip handles 160, 161 may be formed by two identical "halves" that are ultrasonically welded together.

Figure 2A:
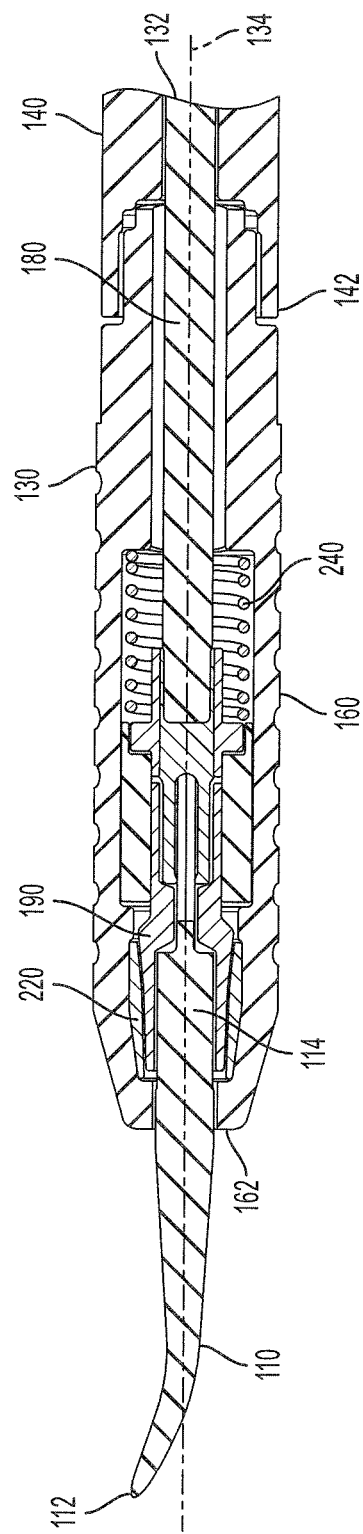
FIG. 2A depicts a partial cross-sectional view of one embodiment of a dental instrument constructed in accordance with one or more aspects of the present invention taken along the line 2-2 in FIGS. 1A and 1n a closed position.
Figure 2B:
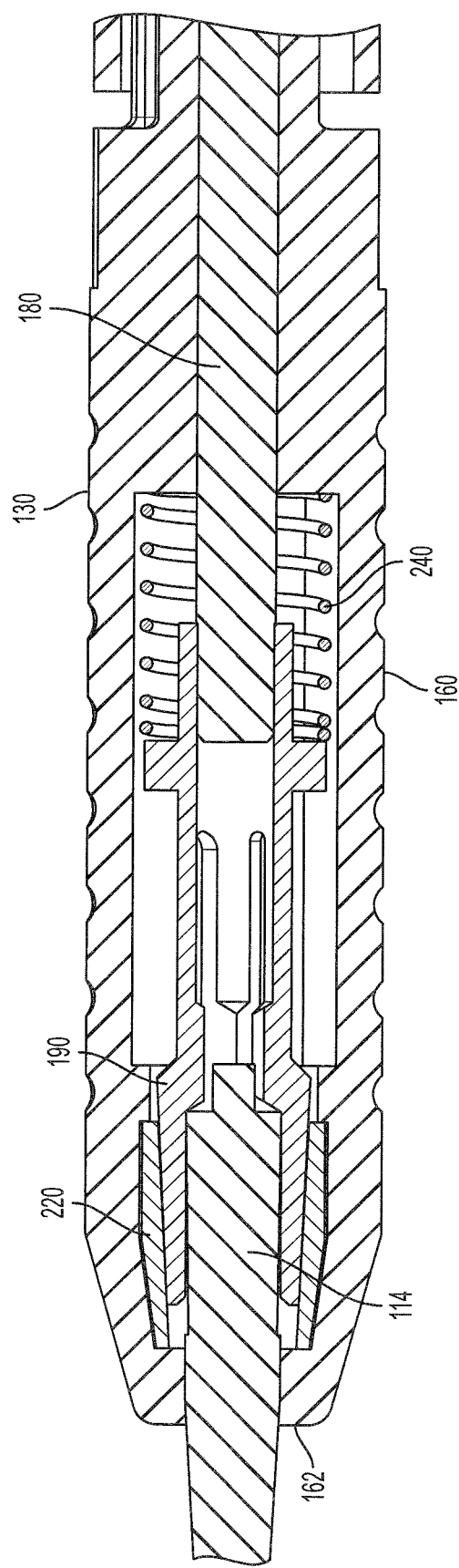
FIG. 2B depicts a partial cross-sectional view of one embodiment of a dental instrument constructed in accordance with one or more aspects of the present invention taken along the line 2-2 in FIGS. 1A and 1n an open position.

As illustrated in FIGS. 2A and 2B, handle 130 includes an internal elongated opening or bore 132 extending through handle center 140 and both grip portions 160, 161 and between a first dental tip entrance 162 formed at an end of a first grip portion 160 and a second dental tip entrance 163 formed at an end of a second grip portion 161. A longitudinal elongated axis 134 extends centrally through internal elongated opening 132 of handle 130. First and second dental tip entrances 162, 163 are configured to receive second end 114 of dental tip 110. In alternative embodiments, handle 130 may only include one grip portion. For simplicity, one side of a dental instrument will be described with the understanding that the same features may be included with a second grip portion extending from the opposing end of handle center 140.

Figure 3A:
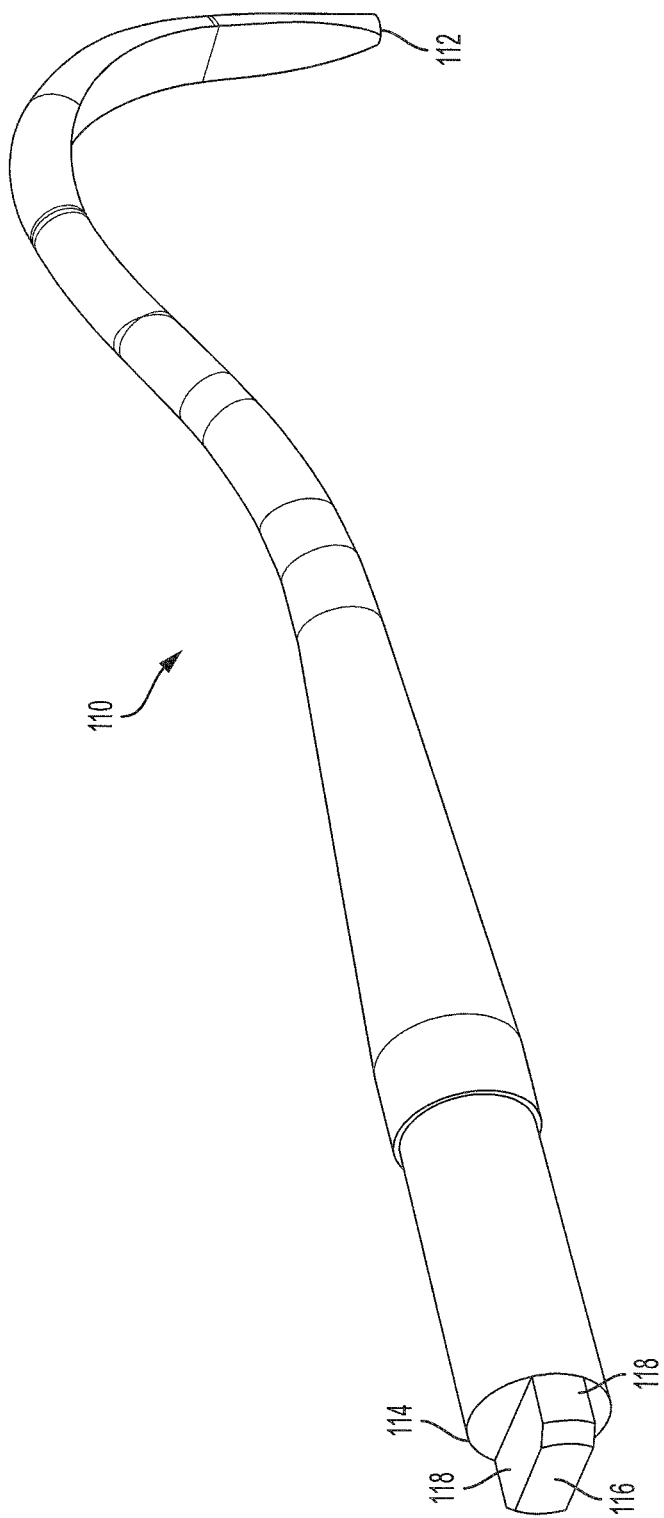
FIG. 3A depicts a perspective view of one embodiment of a dental tip constructed in accordance with one or more aspects of the present invention.
Figure 3B:
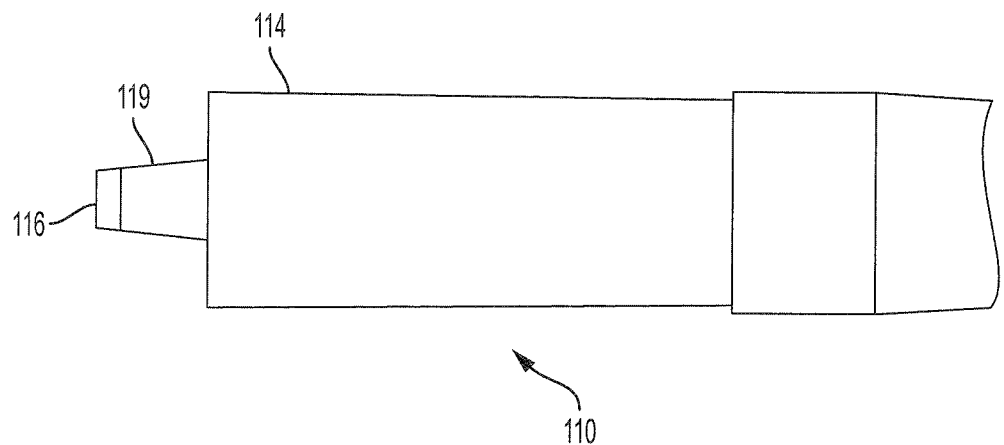
FIG. 3B depicts a side view of another embodiment of a second end of a dental tip constructed in accordance with one or more aspects of the present invention.
Figure 3C:
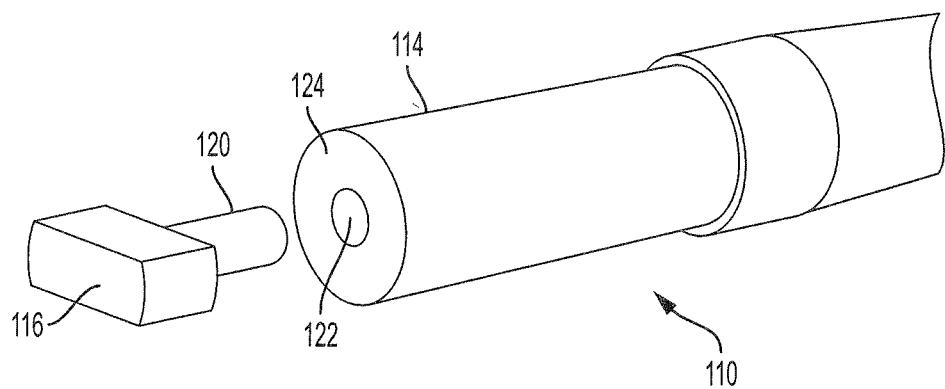
FIG. 3C depicts a perspective view of another embodiment of a second end of a dental tip constructed in accordance with one or more aspects of the present invention.

FIG. 3A illustrates one example of a removable or replaceable dental tip 110 constructed in accordance with one or more aspects of the present invention. Each of dental tips 110 include a first end 112 and a second end 114. First end 112 is the working end of dental tip that, for example, is configured as a scaler, scraper, mouth mirror, reamer, file, chisel, probe, excavator, hollenback, burnisher, scooper, plugger, locator or buffer. First end 112 of each dental tip 110 may be the same as or different from each other. Dental tip 110 may be constructed from, for example, common stainless steel, spring steel, hardened polymers or plastics commonly used in dental applications. Dental tip 110 may be one-piece construction with first end 112 and second end 114 being made from a single piece of material or, alternatively, a two-piece construction. If constructed with two-pieces, working end 112 and butt section 114 may still be one continuous piece and a separate rib 116 (as opposed to a rib integrated with butt section 114) may be equipped with a cylindrical shank or stud that is, for example, press fit, screwed or glued into a blind hole 122 drilled or bored into the end of butt section 114 as illustrated in the example depicted in FIG. 3C.

Second end 114 of dental tip 110 is received and retained within handle 130 as described in more detail below. Second end 114 may be sized and shaped to fit within a slot, area or opening 206 formed in collet 190 as described in more detail below, to prevent the dental tip from rotating relative to axis 134 of handle 130 and to maintain a constant, one hundred and eighty degree (mirrored) relationship with a dental tip 110 on the opposing end of dental instrument 100. In one example, second end 114 may taper radially inward towards first end 112 to enhance retention of second end 114 by collet 190 as described below.

FIG. 3A depicts one example of a second end 114 of dental tip 110 including a rib 116 compatible with first or second dental tip entrances 162, 163 of handle 130. When retained by handle 130, second end 114 of dental tip 110 is constructed to prevent dental tip 110 from rotating in relation to axis 134 of handle 130. In one example, rib 116 includes at least one flat surface 118 to prevent turning or rotation of dental tip 110 relative to axis 134 of handle 130 when retained by handle 130. In alternative embodiments, rib 116 may include two parallel flat or tapered sides 119 (e.g. FIG. 3B). The peripheral sides of rib 116 may be tapered or flat. In yet another embodiment illustrated in FIG. 3C, rib 116 may be a separate element equipped with a shank or stud 120 that is press fit, screwed or glued into a blind hold 122 formed in a terminal end 124 of a butt section of dental tip 110.

Figure 3D:
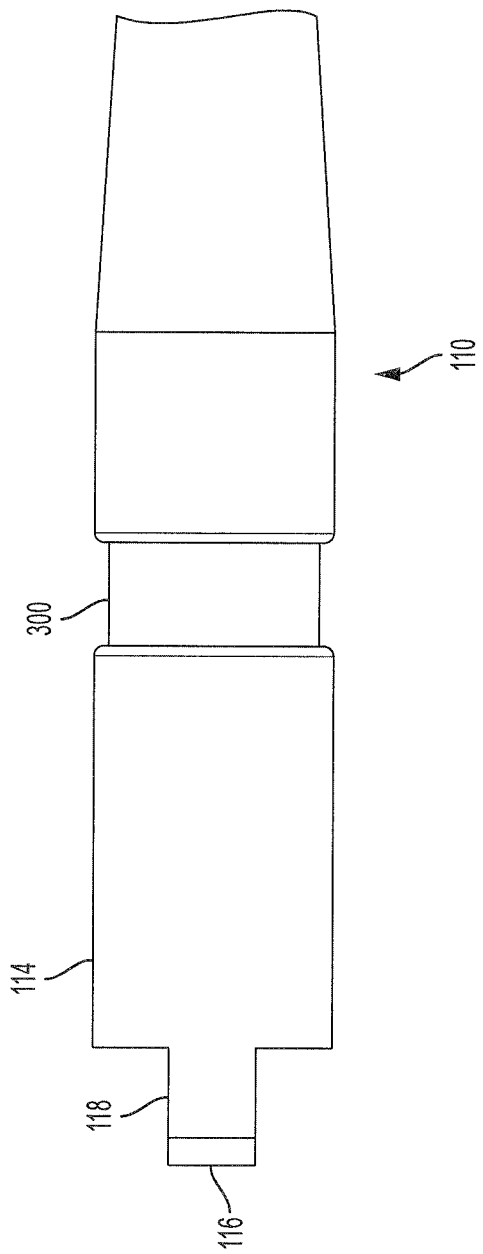
FIG. 3D depicts a side view of another embodiment of a second end of a dental tip constructed in accordance with one or more aspects of the present invention.

Second end 114 of dental tip 110 is retained within handle 130 by, for example, a retaining mechanism that may include an assembly of center rod 180, a collet 190 and a collar 220. In one example illustrated in FIG. 2, center rod 180, collet 190 and collar 220 are axially aligned along elongated axis 134 within internal elongated opening or bore 132 of handle 130. In one embodiment, center rod 180 is affixed to and extends through handle center 140 and into a portion of first and second grip portions 160, 161, and collet 190. Collet 190 and collar 220 are housed within grip portion 160 of handle 130. Second end 114 of dental tip 110 is sized to fit within dental tip entrance 162 of grip portion 160, collet 190, and collar 220. In another example depicted in FIG. 3D, second end 114 may be cylindrical in shape and include a narrow ring or groove 300 machined around its circumference. The ring or groove 300 may be located strategically along axis 134 such that when collet 190 closes down on second end 114, the terminal end of finger portions 202 of spring finger 200 of collet 190 close down on the trailing edge of the ring or groove 300 to enhance retention of dental tip 110.

Figure 4:
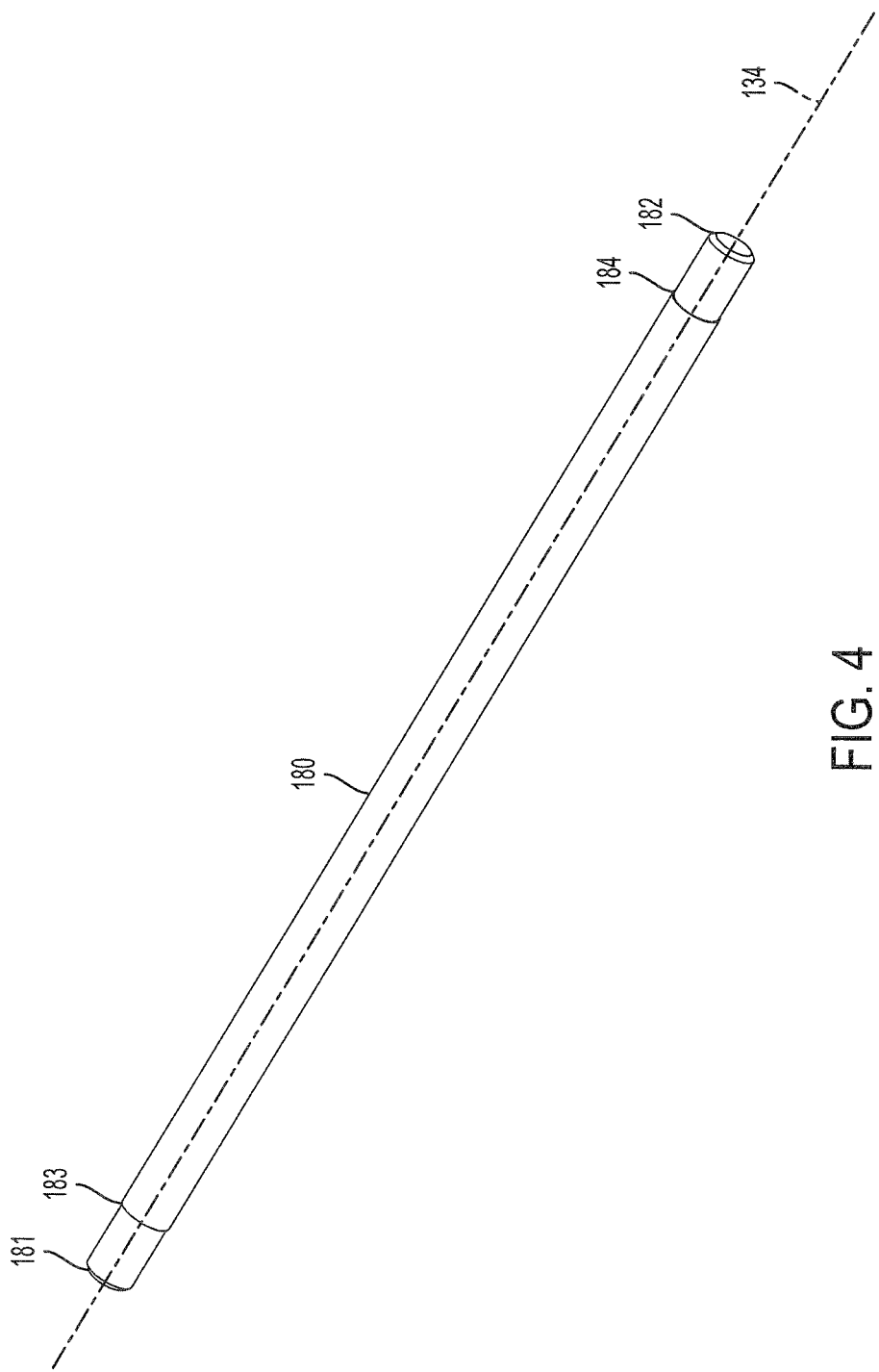
FIG. 4 depicts a perspective view of one embodiment of a center rod constructed in accordance with one or more aspects of the present invention.

In one embodiment illustrated in FIG. 4, center rod 180 is an elongated rod extending along axis 134 having a first end 181 and a second end 182. Center rod 180 may be fabricated from, for example, a metallic, plastic, composite, or polymer material. Center rod 180 is affixed to handle center 140 by, for example, handle center 140 being molded over center rod 180. Alternatively, center rod 180 may be glued, press-fit or attached with a locating pin to handle center 140. Center rod 180 provides concentricity for all of the components of dental instrument 100 and effectively acts as the central axis and support of the entire handle 130. In one example as illustrated in FIG. 4, first and second ends 181, 182 of center rod 180 may include a slight decrease in diameter to create external shoulders 183, 184. Alternatively, second ends 181 and 182 may include external (male) threads for the purpose of joining to end 193 of collet 190.

Figure 5A:
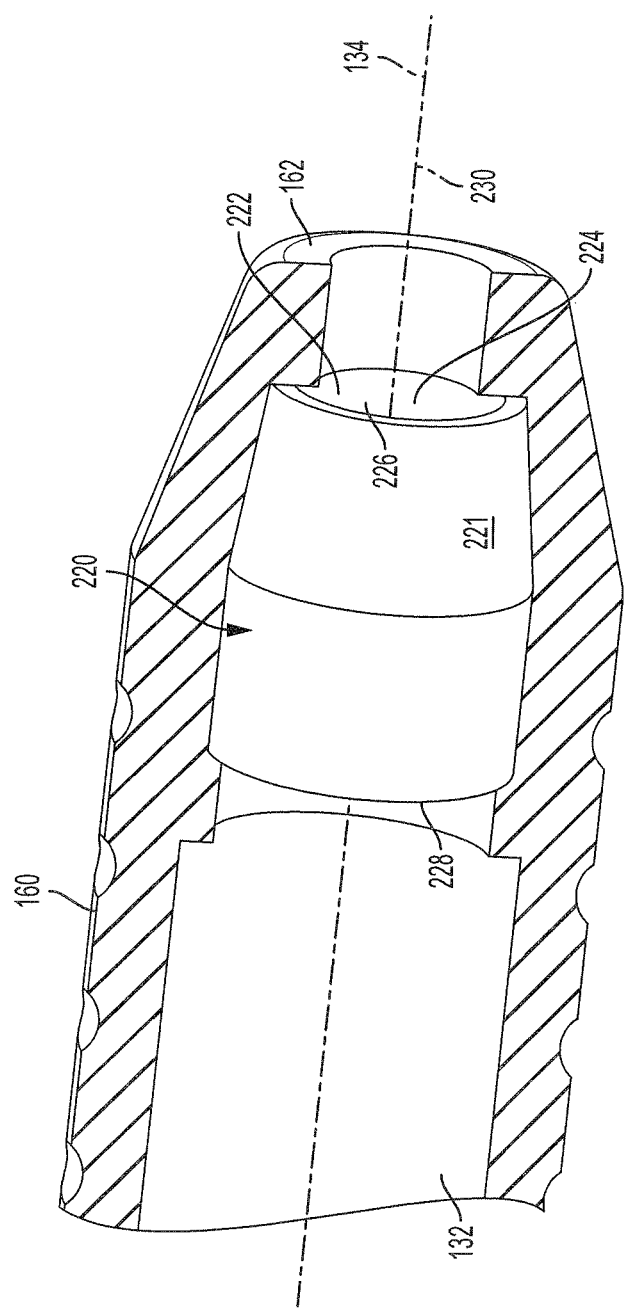
FIG. 5A depicts a perspective view of one embodiment of a collar positioned within a grip portion (cross-sectional view) near a dental tip entrance constructed in accordance with one or more aspects of the present invention.

FIG. 5A illustrates one example of collar 220. In this example, collar 220 is fixed or nested within the elongated opening 132 of handle 130 near dental tip entrance 162 of grip portion 160. Collar 220 is restricted in its axial movement by, for example, internal locating shoulders within grip portion 160 or, alternatively, being press fit or screwed within elongated opening 132 of grip portion 160. In another embodiment, collar 220 may be molded into grip portion 160 during the plastic injection molding process instead of being inserted during assembly of dental instrument 100. Collar 220 may be constructed from, for example, stainless steel or other metallic or polymer materials. Externally, collar 220 is cylindrical in shape and may include a chamfered end 221 to provide for the greatest possible wall-thickness at a tapered end of grip portion 160. As illustrated in FIG. 5A, collar 220 includes an internal surface 222 that defines a bore 224 having a longitudinal axis 230 aligned with and extending along axis 134 of handle 130 from a first cylindrical opening 226 proximate dental tip entrance 162 of grip portion 160 and a second cylindrical opening 228 facing second grip portion 160. Internal surface 222 of bore 224 of collar 220 may, in one example, taper radially outward from elongated axis 134 of handle 130 and away from dental tip entrance 162 of grip portion 160.

Figure 5B:
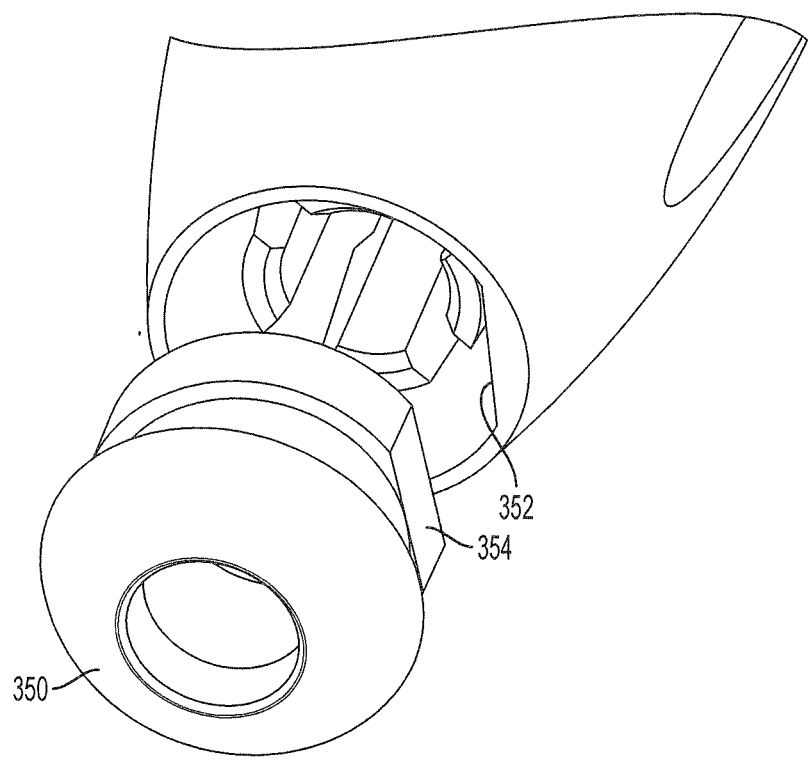
FIG. 5B depicts a perspective view of another embodiment of a collar constructed in accordance with one or more aspects of the present invention.
Figure 5C:
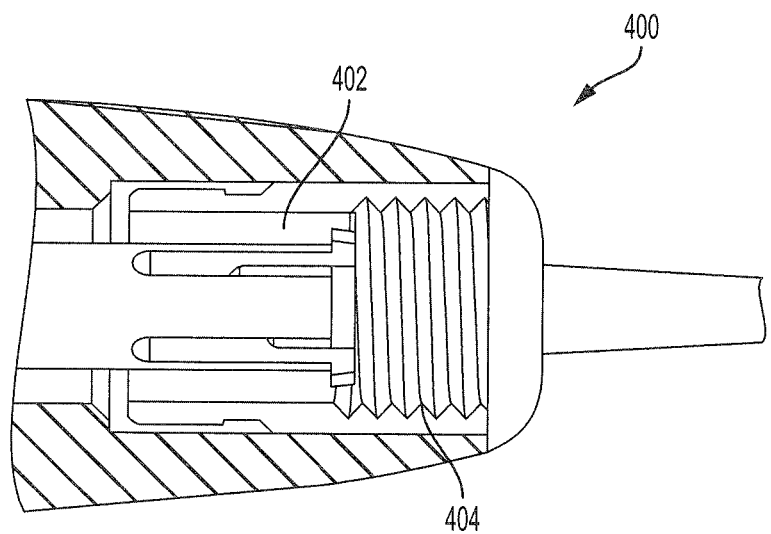
FIG. 5C depicts a side view of another embodiment of a collar constructed in accordance with one or more aspects of the present invention.

In an alternative embodiment illustrated in FIG. 5B, collar 350 may be retained by a "twist-lock" feature. In this example, an external shoulder 354 on the collar engages with an internal tab 352 on grip portion 160 to retain the collar inside grip portion 160 when it is pressed into dental tip entrance 162 and rotated. In yet another embodiment illustrated in FIG. 5C, collar 400 may be of two-piece construction including a sleeve 402 with an internal (female) thread that is press fit into dental tip entrance 162 of grip portion 160 up to, for example, an internal locating shoulder, and an insert 404 with an internal taper and external (male) thread that screws into sleeve 402. When insert 404 is threaded into sleeve 402, the exposed portion of insert 404 may include a slit or channel that is compatible with common flat-head screw drivers and/or coins that may be used to remove the threaded insert and access other internal components for maintenance or cleaning purposes. In yet another embodiment, a collar may be inserted through dental tip entrance 162 by press-fitting or gluing, using, for example, Loctite® glue, into dental tip entrance 162 up to an internal locating shoulder within grip portion 160. In yet another embodiment, collar may be integrated into grip portion 160 instead of being a separate component housed therein.

FIG. 6 illustrates one example of collet 190 constructed in accordance with one or more aspects of the present invention. Collet 190 extends along axis 134 of handle 130. Collet 190 may include a body portion 192, spring fingers 200 extending axially from body portion 192 and a raised shoulder 194 separating body portion 192 and spring fingers 200. The opposing end 193 of body portion 190 may be fixed to an end 182 of center rod 180. End 193 of body portion 192 may include a cavity to receive end 182 of center rod 180. Body portion 192 may be, for example, press fit, glued or screwed onto end 182 of center rod 180. In one example, body portion 192 is glued to center rod 180 using, for example, Loctite® glue. When collet 190 is press fit or glued onto center rod 180, external shoulders 183, 184 of center rod 180 may act as a hard stop to ensure proper longitudinal positioning of collet 190. In an alternative embodiment, body portion 192 of collet 190 may extend into handle center 140, which would eliminate the need for a separate center rod 180. In this example, body portion 192 of collet 190 would be elongated and extend and be, for example, press-fit or glued, into handle center 140. In yet another embodiment, center rod 180 may be a two-part construction, instead of a single center rod extending throughout the entire handle center 140 and into the two grip portions 160, 161 as depicted in FIG. 4. In this example, one end of each distinct center rod may be press-fit or molded into ends 142, 143 of handle center 140 and the other end would be affixed to end 193 of body portion 192 of collet 190 as described above.

Spring finger 200 of collet 190 includes a flexible base 208 and resilient finger portions 202 extending axially along elongated axis 134 of handle 130 towards dental tip entrance 162. Finger portions 202 define an outer surface 204 having an outer diameter sized for slidable engagement with internal surface 222 of collar 220. Outer surface 204 of spring fingers 200 may match internal surface 222 of bore 224 of the collar 220. For example, a portion of outer surface 204 of finger portions 202 may be conically tapered and is surrounded by and engages internal surface 222 of collar 220 as spring fingers 200 slide axially towards dental tip entrance 162 of grip portion 160.

Internally, spring finger 200 defines a space, opening or area 206 for allowing radial inward movement of finger portions 202. Area 206 may be shaped as a cylindrical bore extending from an end 195 of collet 190 to a prescribed blind depth. Finger portions 202 are moveable radially inward and outward between an open position and a closed position depending on the axial location along axis 134 of collet 190 relative to collar 220. As finger portions 202 slide axially towards dental tip entrance 162 of grip portion 160, finger portions 202 are urged radially inward toward elongated axis 134 as a result of the engagement of outer surface 204 of spring fingers 202 with internal surface 222 of bore 224 of collar 220. Second end 114 of dental tip 110 is configured to be insertable inside of area 206 formed between spring fingers 200. The depth of area 206 along axis 134 may restrict the extent to which second end 114 of dental tip 110 can be inserted into collet 190. Second end 114 of dental tip 110 is retained by finger portions 202 within this area 206 when finger portions 202 are in the closed position and removable from this area 206 when finger portions 202 are in the open position.

Figure 7:
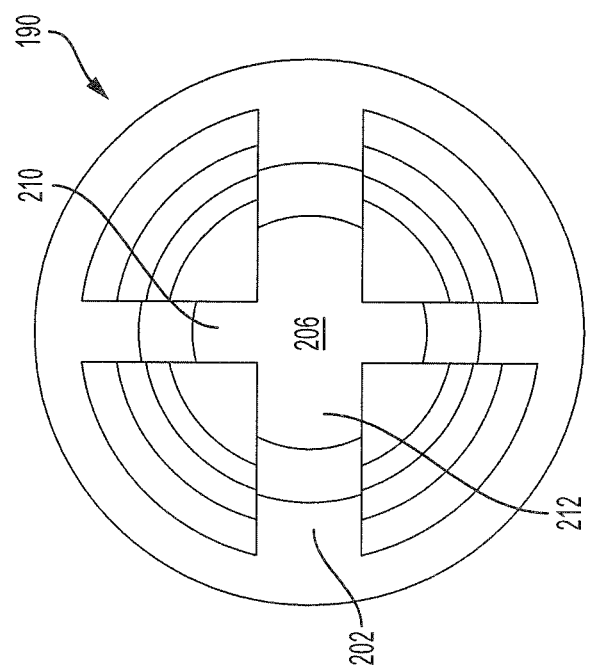
FIG. 7 depicts an end view of one embodiment of a collet constructed in accordance with one or more aspects of the present invention.

Collet 190 may also be "back drilled" with another internal bore extending from an end of spring fingers 200 to a prescribed depth. The purpose of this hole is to reduce the cross-sectional area of spring fingers 200, thereby decreasing their rigidity. Slots may also run longitudinally along collet 190, in conjunction with the internal bore, to assist in forming spring fingers 200 that retain dental tip 110. In this example, the "slots" may refer to a cut through both sidewalls of collet 190 resulting in two slits or channels of uniform width on opposite sides of collet 190 (180 degrees opposed) that extend from an end of spring fingers 200 to some prescribed length along axis 134. In one example illustrated in FIG. 7, collet 190 may include two such slots 210, 212, oriented ninety degrees from one another around the circumference of collet 190. This creates four slits or channels, and correspondingly four uniform finger portions 202 at an end of collet 190. One slot may be wider than the other. The width of the wider slot may match the distance between flat surfaces 118 of rib 116 (e.g. the height of rib 116). As dental tip 110 is inserted into dental tip entrance 162 of grip portion 160, a user can rotate dental tip 110 while applying an axial force until the flat surface of rib 116 seats or locates into the wider of the two slots.

In one embodiment of dental instrument 100 shown in FIGS. 2A and 2B, a helical compression spring 240 may be used to normally urge collet 190 in an axial direction along elongated axis 134 of handle 130 towards dental tip entrance 162 of the grip portion 160 and into engagement with collar 220. Spring 240 may be under constant compression. As a support for spring 240, collet 190 may include a raised shoulder 194 which may be positioned on body portion 192 near base 208 of spring fingers 200 of collet 190. Shoulder 194 may include a surface 196 facing away from dental tip entrance 162 of grip portion 160. One end of spring 240 may be held stationary by shoulder 194, such as, for example, a surface of shoulder 194, while the other end of spring 240 applies force to an end surface 172 within elongated opening 132 of grip portion 160, which urges spring finger 200 of collet 190 to slidably engage collar 220. When dental instrument 100 is assembled and in a closed (or locked) position, the distance between surface 196 of shoulder 194 and back end surface 172 of grip portion 160 is shorter than the uncompressed length of spring 240 which causes spring 240 to be under constant compression resulting in the biasing toward collar 220. As a result, grip portion 160 is forced toward handle center 140, which causes collar 220 to engage outer surface 204 of finger portions 202 of spring fingers 200. Spring 240 may be made using a variety of materials, such as stainless steel, wire diameters, spring lengths and spring rates, and is only limited by the size constraints imposed by the internal dimensions of grip portion 160.

Figure 8:
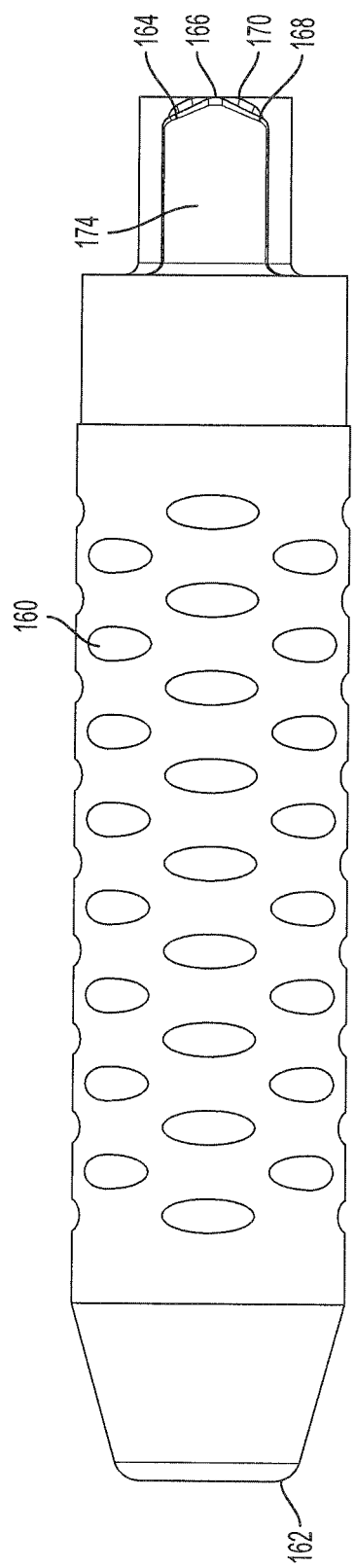
FIG. 8 depicts a side view of one embodiment of a grip portion constructed in accordance with one or more aspects of the present invention.
Figure 9:
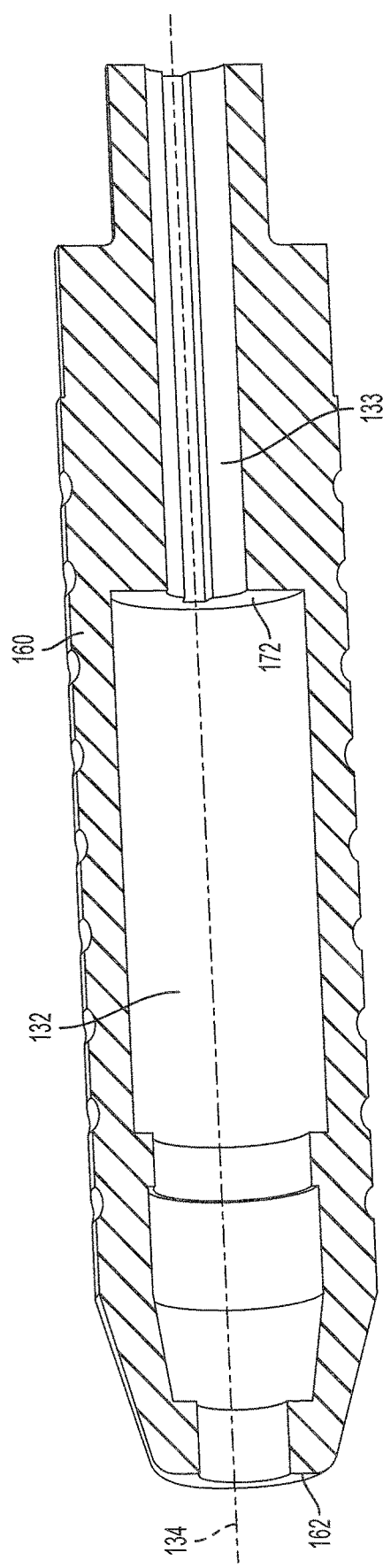
FIG. 9 depicts a side view of one embodiment of one half of a grip portion constructed in accordance with one or more aspects of the present invention.
Figure 10:
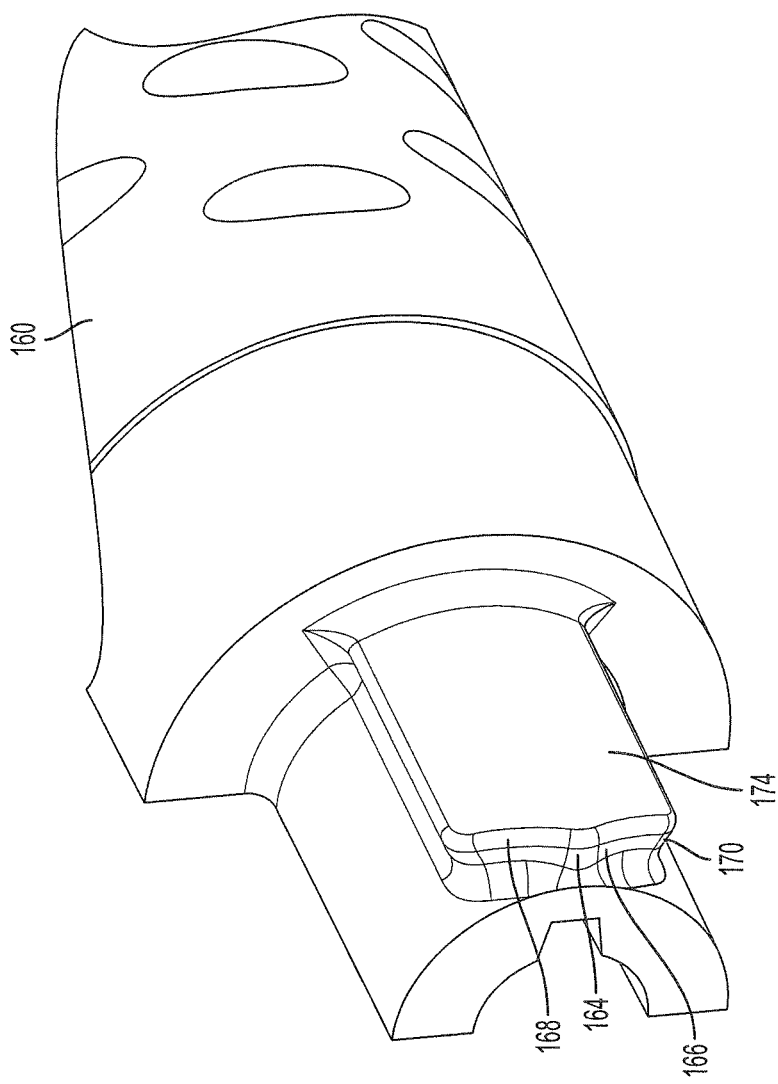
FIG. 10 depicts a partial perspective view of one embodiment of an end of a grip portion illustrating one example of a cam follower of a grip portion constructed in accordance with one or more aspects of the present invention.

One embodiment of a grip portion constructed in accordance with one or more aspects of the present invention is depicted in FIGS. 8-10. Grip portion 160 may be injected molded using, for example, a PPSU resin and include a knurled outer surface. As illustrated in FIG. 2, for example, grip portion 160 houses collar 220, collet 190, spring 240, and a portion of center rod 180. Grip portion 160 includes a dental tip entrance 162 at one end and a hole or bore 133 at the other end. Bore 133 provides a bearing surface for center rod 180. In one embodiment, bore 133 may include, for example, additional material removed to create a venting channel that allows steam to penetrate the device more easily during the sterilization process.

Figure 11B:
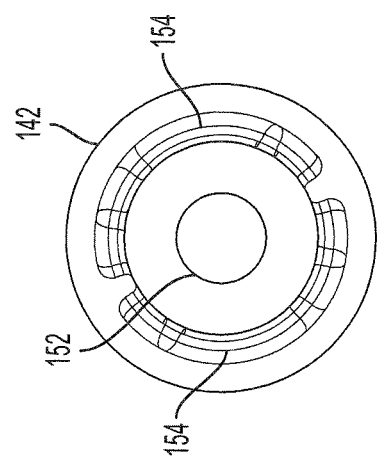
FIG. 11B depicts an end view of a handle center constructed in accordance with one or more aspects of the present invention.
Figure 11A:
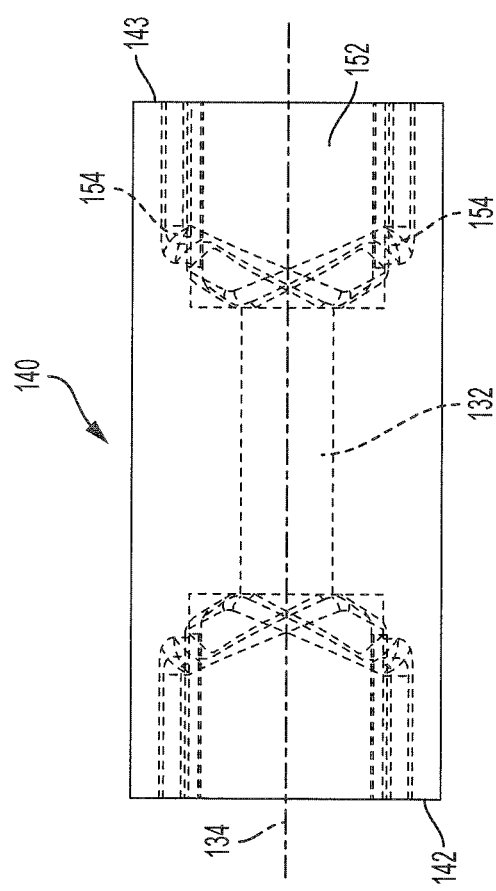
FIG. 11A depicts a side transparent view of one embodiment of a handle center constructed in accordance with one or more aspects of the present invention, wherein the dashed lines illustrate one example of camming surfaces within a cavity at an end of handle center.

FIGS. 11A and 11B illustrate one example of a handle center 140 constructed in accordance with one or more aspects of the present invention. Handle center 140 includes two ends 142, 143 and may be over-molded onto center rod 180, which passes through elongated opening 132, at the center of center rod 180.

In accordance with one or more aspects of the present invention, rotation of grip portion 160 relative to handle center 140 causes grip portion 160 to move either away from or towards handle center 140 along axis 134 depending on the direction of rotation. In one example, this translational movement along axis 134 is achieved by a cam mechanism. When grip portion 160 is rotated relative to handle center 140, opposing camming surfaces on grip portion 160 and handle center 140 engage and cause grip portion 160 to move along axis 134 relative to handle center 140.

One example of a cam mechanism causing this translational movement is depicted in FIGS. 10-13. In this example, grip portion 160 includes a follower 174, illustrated in FIGS. 8 and 10, on its back end, opposite dental tip entrance 162, and handle center 140 includes a cylindrical cavity 152 including a circumferential contour cut into the internal surface of cavity 152 illustrated in FIGS. 11A and 11B. In one example, follower 174 may include an extruded arrow-shaped surface. The circumferential contour cut on the internal surface of cavity 152 of handle center 140 creates a cam path 154. In one example, cam path 154 includes sections that incline and section that decline. In one example, the pitch of these sections may be 62.5 degrees, however a range of pitches and angles may be used. Cam path 154 may be filleted on all edges to help reduce wear and improve machinability. In an alternative embodiment, a cam path may be formed on an external surface of handle center 140 and a cam follower may be formed on an internal surface of a cavity in grip portion 160. In yet another alternative embodiment, a cam path may be formed on the internal cavity of grip portion 160 and a cam follower may be on an external surface of handle center 140. In yet another alternative embodiment, a cam path may be formed on an external surface of grip portion 160 and a cam follower may be formed on an internal surface of a cavity on handle center 140.

Follower 174 of grip portion 160 interacts with and engages cam path 154 of handle center 140 to cause translation of grip portion 160 along axis 134 in relation to handle center 140. Handle center 140 remains stationary while grip portion 160 is rotated causing follower 174 to be guided by cam path 154, which moves grip portion 160 longitudinally along axis 134 and center rod 180. When grip portion 160 is rotated relative to handle center 140, follower 174 is guided by the profile of cam path 154. The cam path's pitch causes grip portion 160 to move either away from or towards handle center 140 depending on the direction of rotation.

Figure 12:
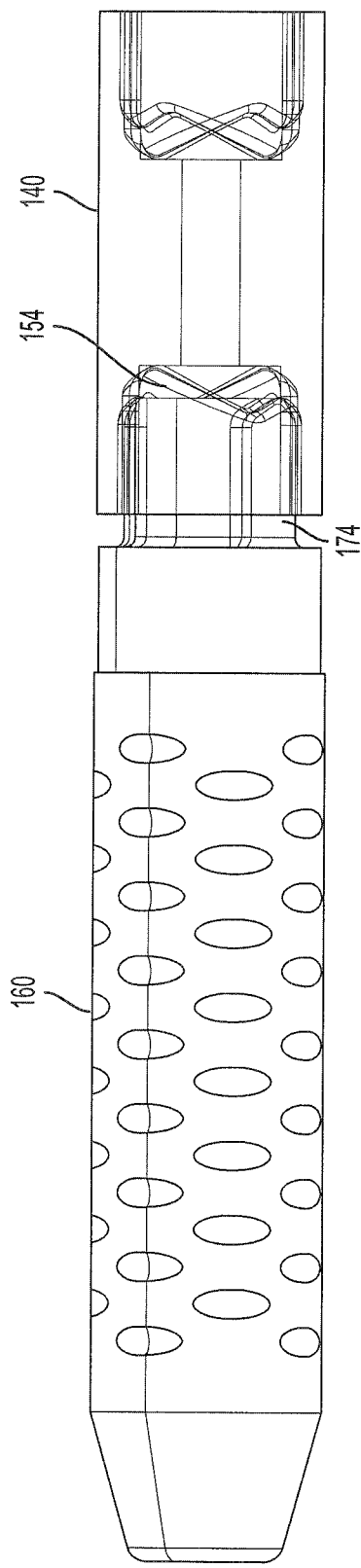
FIG. 12 depicts a partial side transparent view of one embodiment of a dental instrument constructed in accordance with one or more aspects of the present invention in an open position, wherein the dashed lines illustrate one example of camming surfaces within a cavity at an end of handle center.

When grip portion 160 is rotated relative to handle center 140 to an open or "unlocked" position, as illustrated in FIG. 12, the interfacing cam or engagement surfaces of follower 174 and cam path 154 cause spring 240 to compress even more as grip portion 160 moves away from handle center 140. At that same time, the internal taper of internal surface 222 of collar 220 disengages from outer surface 204 of finger portions 202 of spring finger 200 of collet 190 and increases area 206 between finger portions 202 allowing second end 116 of dental tip 110 to be freely inserted or withdrawn. As follower 174 is guided by cam path 154, the pitch of the cam causes grip portion 160 to move away from handle center 140. At, for example, seventy-seven degrees from the zero position, follower 174 is at the peak of cam path 154 and grip portion 160 is at its furthest from handle center 140. As the user continues to turn grip portion 160 clockwise, the cam pitch begins to decline and causes grip portion 160 to move back towards handle center 140. At, for example, one hundred and seven degrees, grip portion 160 cannot rotate any further due to the cam profile and is now seated in the open or "unlocked" position at a distance offset from handle center 140. This offset distance ensures that collar 220 within grip portion 160 is not engaged with finger portions 202 of spring finger 200 of collet 190 while dental instrument 100 is in the open or "unlocked" position.

Figure 13:
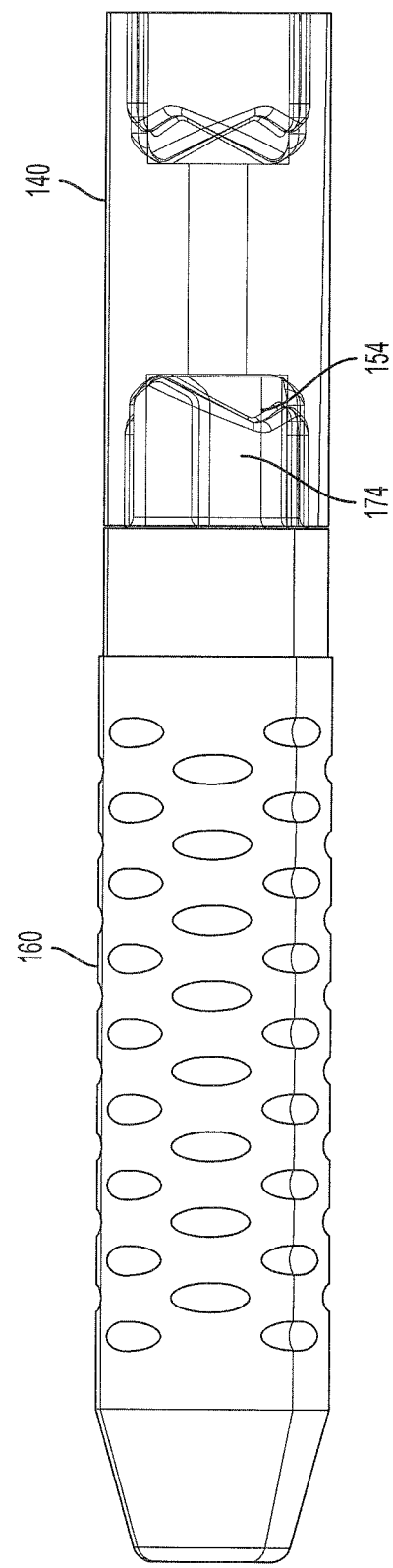
FIG. 13 depicts a partial side transparent view of one embodiment of a dental instrument constructed in accordance with one or more aspects of the present invention in a closed position, wherein the dashed lines illustrate one example of camming surfaces within a cavity at an end of handle center.
Figure 14:
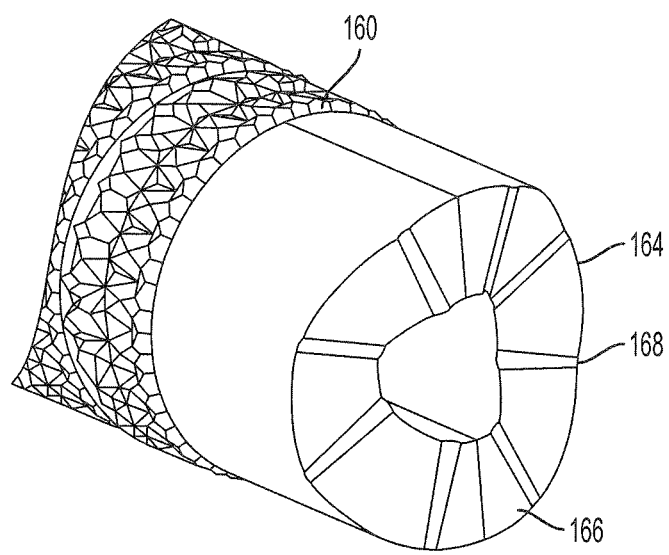
FIG. 14 depicts a partial perspective view of an alternative end of a grip portion illustrating an engagement surface constructed in accordance with one or more aspects of the present invention.
Figure 15:
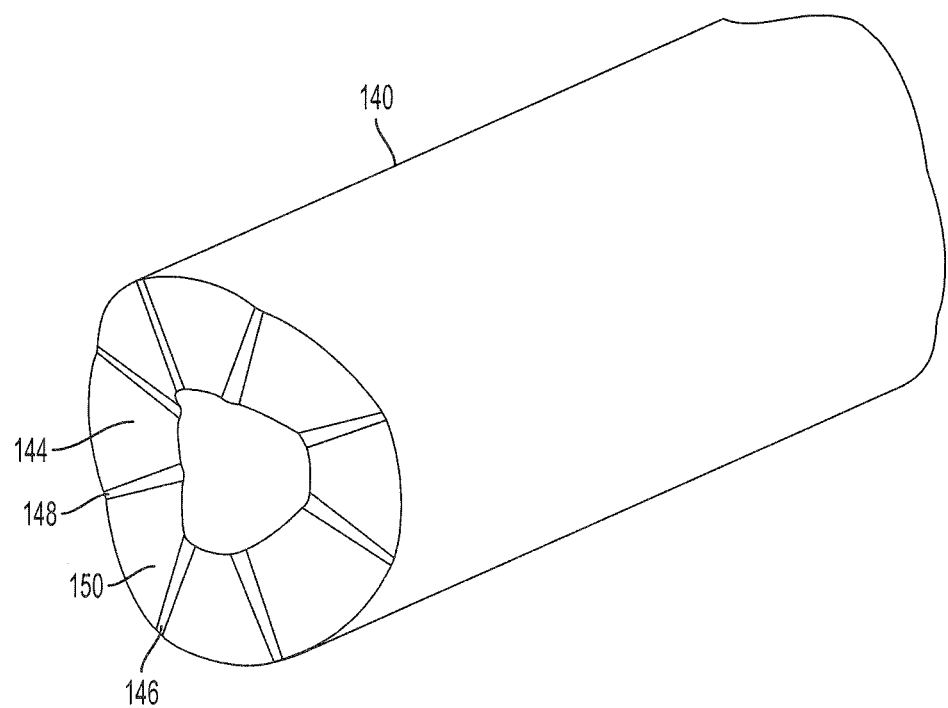
FIG. 15 depicts a partial perspective view of an alternative end of a handle center illustrating an engagement surface constructed in accordance with one or more aspects of the present invention.
Figure 16A:
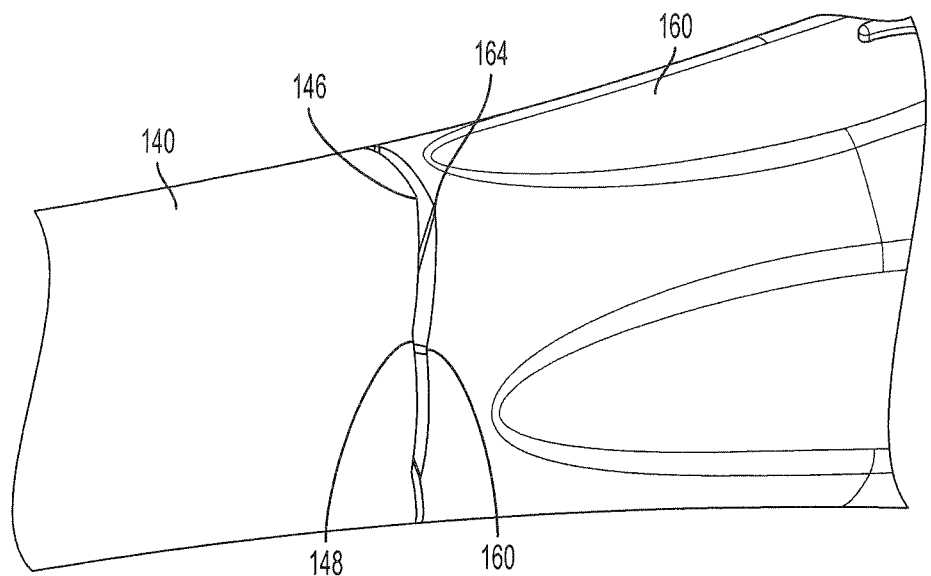
FIG. 16A depicts a perspective view of one embodiment of a dental instrument constructed in accordance with one or more aspects of the present invention in a closed position.
Figure 16B:
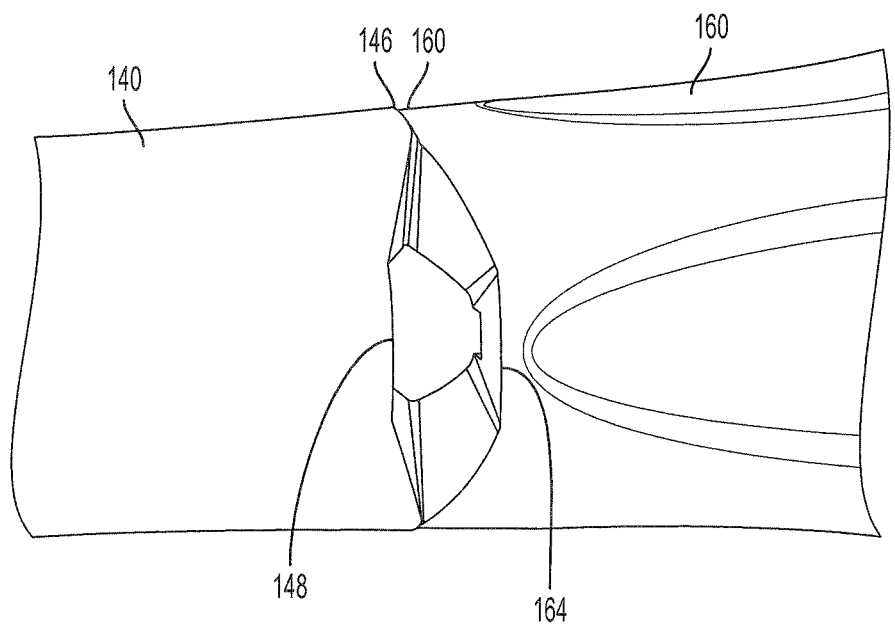
FIG. 16B depicts a perspective view of one embodiment of a dental instrument constructed in accordance with one or more aspects of the present invention in an open position.

To close or "lock" dental instrument 100, as illustrated in FIG. 13, a user rotates grip portion 160 counter-clockwise, forcing follower 174 of grip portion 160 to follow cam path 154 in reverse (e.g. gradually moving away from handle center 140 to the peak of the cam and then back towards handle center 140 until it is seated in the closed or "locked" position). Variations in the components of the cam mechanism may be used including, for example, a follower 174 including different widths and thickness, steeper or shallower counter angles of cam path 154, a relief added to the bottom of cam path 154 to ensure that follower 174 does not bottom out when dental instrument 100 is in the closed or "locked" position.

In an alternative embodiment illustrated in FIGS. 14, 15, 16A and 16B, dental instrument 100 may use inclined surfaces at opposing ends of grip portion 160 and handle center 140 in place of follower 174 of grip portion 160 and recessed cam path 154 of handle center 140. In this example, end 142 of handle center 140 includes an engagement surface 144 facing an engagement surface 164 of grip portion 160 opposite dental tip entrance 162. Engagement surface 144 of handle center 140 engages and is rotatable relative to engagement surface 164 of grip portion 160. Rotation of grip portion 160 in relation to handle center 140, in either direction, causes axial movement along axis 134 of grip portion 160 away from or towards handle center 140. Since center rod 180 is fixed to handle center 140 and collet 190, translation of grip portion 160 along axis 134 away from or towards handle center 140 resulting from rotation of grip portion 160 relative to handle center 140 will cause collet 190 to disengage or engage collar 220 depending on the axial location of grip portion 160 along axis 134 in relation to handle center 140.

As grip portion 160 is rotated relative to handle center 140 in either direction, grip portion 160 translates axially along elongated axis 134 of handle 130 causing the position of collet 190 to be closer to or farther away from dental tip entrance 162 of grip portion 160 depending on interaction and interface of engagement surface 164 of grip portion 160 and engagement surface 144 of handle center 140. As grip portion 160 moves axially along elongated axis 134 of handle 130 causing collet 190 to be closer to dental tip entrance 162 of grip portion 160 caused by rotation of grip portion 160 relative to handle center 140, internal surface 222 of bore 224 of collar 220 engages outer surface 204 of finger portions 202 of spring finger 200 of collet 190 and urges finger portions 202 radially inward towards axis 134 into the closed position (e.g. FIG. 16A) for retaining second end 114 of dental tip 110. As grip portion 160 moves axially along elongated axis 134 of handle 130 causing the position of collet 190 to be farther away from dental tip entrance 162 caused by rotation of grip portion 160 relative to handle center 140 in either direction, internal surface 222 of bore 224 of collar 220 disengages, or lessens the compression or urging on, outer surface 204 of finger portions 202 and allows finger portions 202 to move radially outward from axis 134 into the open position (e.g. FIG. 16B) for permitting removal or insertion of second end 114 of dental tip 110.

Engagement surface 144 at end 142 of handle center 140 interacts with and engages engagement surface 164 of grip portion 160. In one example, engagement surface 144 of handle center 140 includes a series of inclined planes with peaks 146 and valleys 148, and engagement surface 164 of grip portion 160 includes a series of inclined planes with peaks 166 and valleys 168. When a peak 166 of engagement surface 164 of grip portion 160 aligns with or is rotated towards a peak 146 of engagement surface 144 of handle center 140 during rotation of grip portion 160 relative to handle center 140, grip portion 160 will translate along axis 134 away from handle center 140. When a peak 166 of engagement surface 164 of grip portion 160 aligns with or moves towards a valley 148 of engagement surface 144 of handle center 140, or alternatively a valley 168 of engagement surface 164 of grip portion 160 aligns with a peak 146 of engagement surface 144 of handle center 140, during rotation of grip portion 160 relative to handle center 140, grip portion 140 will translate along axis 134 towards handle center 140. In one example, engagement surfaces 144, 146 may include inclined or angulated surfaces extending between each peak 146, 166 and valley 148, 168 to allow smooth transitions during rotation.

In one example of use of a dental instrument 100 constructed in accordance with one or more aspects of the present invention, a dental tip 110 is inserted into dental instrument 100 by first rotating grip portion 160 relative to handle center 140 in either direction. Grip portion 160 is rotated relative to handle center 140 to align or engage peak 146 of engagement surface 144 at end 142 of handle center 140 with peak 166 of engagement surface 164 of grip portion 160. Alignment of these peaks 146, 166 causes grip portion 160 to move away from or axially translate along elongated axis 134 from handle center 140. This axial translation of grip portion 160 from handle center 140 causes collet 190 to slide axially away from dental tip entrance 162. As collet 190 slides axially away from dental tip entrance 162, compression on outer surface 204 of finger portions 202 caused by internal surface 222 of bore 224 lessens and causes finger portions 202 to separate, open up or radially move away from elongated axis 134 and widen area 206. As finger portions 202 separate, second end 114 of dental tip 110 may be inserted into dental tip entrance 162 and area 206 formed between finger portions 202. Once second end 114 of dental tip 110 is fully seated in area 206 between finger portions 202, grip portion 160 is again rotated relative to handle center 140 to align or engage peak 146 of engagement surface 144 of handle center 140 with valley 168 of engagement surface 164 of grip portion 160, or alternatively, align or engage valley 148 of engagement surface 144 of handle center 140 with peak 168 of engagement surface 164 of grip portion 160. During this rotation, grip portion 160 moves along axis 134 towards handle center 140 causing collet 190 to axially move along axis 134 towards dental tip entrance 162 and into, or further into, collar 220. As collet 190 moves further into collar 220, internal surface 222 of bore 224 applies radial compression or urges outer surface 204 of finger portions 202 radially inwardly which causes the inner surfaces of finger portions 202 to close around and against rib 116 of second end 114 of the dental tip 110 to retain second end 114 of dental tip 110. In one embodiment, finger portions 202 may also grip onto the outer circumference of end 114 of dental tip 110.

In one example, a dental tip 110 is removed from dental instrument 100 by rotating grip portion 160 relative to handle center 140 (in either direction). Grip portion 160 is rotated relative to handle center 140 to align or engage peak 146 of engagement surface 144 at end 142 of handle center 140 with peak 166 of engagement surface 164 of grip portion 160. Alignment of peaks 146, 166 causes grip portion 160 to move along elongated axis 134 away from handle center 140. This movement of grip portion 160 away from handle center 140 causes spring finger 200 of collet 190 to slide axially away from dental tip entrance 162 since collet 190 is fixed to center rod 180, which is fixed to handle center 140. As spring fingers 200 slide axially away from dental tip entrance 162, compression on outer surface 204 of finger portions 202 of spring finger 200 caused by internal surface 222 of bore 224 of collar 220 lessens and causes finger portions 202 of spring finger 200 of collet 190 to separate, open up or radially move away from elongated axis 134 of handle 130. As finger portions 202 separate and area 206 formed by finger portions 202 increases, second end 114 of dental tip 110 may be removed from area 206. At this time, a new dental tip may be inserted and retained as described above.

Figure 17A:
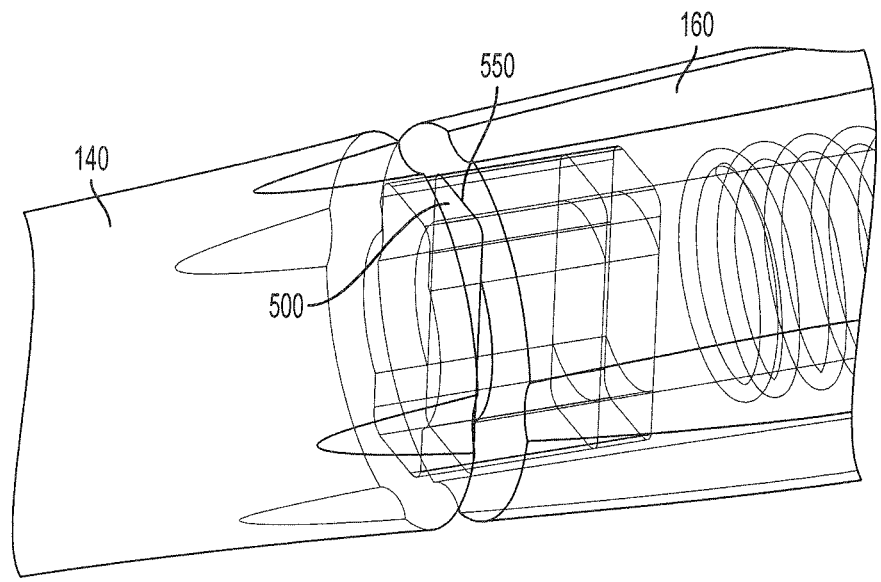
FIGS. 17A and 17B depict perspective views of alternative embodiments of a dental instrument constructed in accordance with one or more aspects of the present invention.
Figure 17B:
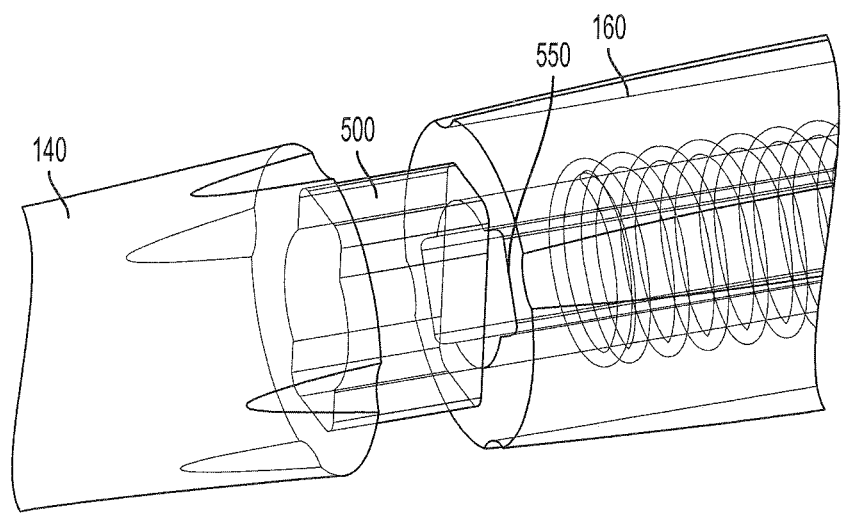
Figure 18A:
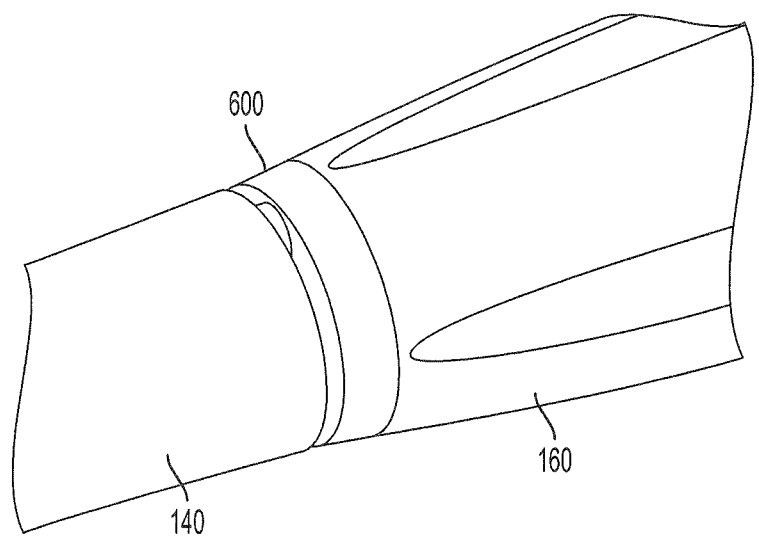
FIGS. 18A and 18B depict perspective views of alternative embodiments of a dental instrument constructed in accordance with one or more aspects of the present invention.
Figure 18B:
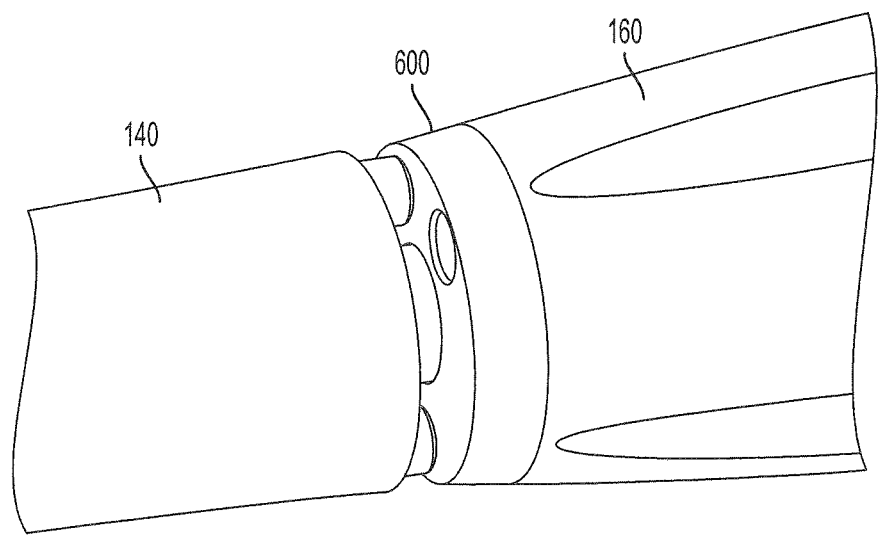

Several other configurations may be used to open/unlock or close/lock dental instrument 100 instead of the cam mechanism described above. As shown in FIGS. 17A and 17B, dental instrument 100 may include the use of "keyed" offset surfaces 500, 550 in place of the cam mechanism to hold grip portion 160 in the open or "unlocked" position. In this example, grip portion 160 is held by a user and pushed away from handle center 140 until spring 240 is fully compressed in order to open or "unlock" the instrument. The user then rotates grip portion 160 in either direction until the offset surfaces are bearing on each other. To close or "lock" dental instrument 100, grip portion 160 is twisted again in either direction until the offset surfaces are no longer bearing or in contact with each other. In another example illustrated in FIGS. 18A and 18B, an insert 600 made from, for example, metal or plastic, may be glued or press fit into a tail end of grip portion 160. This insert includes holes which interface with pins that are pressed into the end of handle center 140. Similar to the offset surfaces described above, a user pushes grip portion 160 forward (i.e. away from handle center 140) and twists (in either direction) to open or "unlock" dental instrument 100 to allow for dental tip insertion or removal. Twisting grip portion 160 until the holes align with the pins will allow grip portion 160 to move toward handle center 140 and will "lock" dental instrument 100 in a closed position, thus retaining end 114 of dental tip 110 within dental instrument 100.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A dental instrument, said dental instrument comprising:
   a dental tip, said dental tip including a first end and a second end;
   a handle, said handle including a handle center and a grip portion, said handle including an axis and an elongated opening extending along the axis though the handle center and the grip portion, the handle center including a first surface, wherein the first surface of the handle center includes multiple inclined plane surfaces, the grip portion including a dental tip entrance end and a second surface in engagement with the first surface of the handle center, wherein the second surface of the grip portion includes multiple inclined plane surfaces, the second surface of the grip portion being rotatable about the axis relative to the first surface of the handle center, wherein rotation of the second surface of the grip portion relative to the first surface of the handle center causes translation along the axis of the grip portion relative to the handle center between a first axial position and a second axial position;
   a collar, said collar disposed within the elongated opening proximate the dental tip entrance end of the grip portion, said collar including a bore extending along the axis between a first opening proximate to and aligned with the dental tip entrance end of the grip portion and a second opening; and
   a collet, said collet including a body portion and spring fingers extending from the body portion, the spring fingers including a dental tip retaining portion configured to receive the second end of the dental tip, the spring fingers being urged radially inward by said collar towards the axis to secure the second end of said dental tip when the grip portion is in the first axial position relative to the handle center, the second end of said dental tip being removable from the dental tip retaining portion of the spring fingers of said collet when the grip portion is in the second axial position relative to the handle center; and
   a center rod, said center rod extending along the axis, at least a portion of said center rod affixed to the handle center, said center rod including an end affixed to the body portion of said collet.

2. The dental instrument of claim 1, further comprising a spring housed within the grip portion, said spring engages the grip portion for urging the dental tip entrance end of the grip portion axially toward the dental tip retaining portion of the spring fingers of said collet.

3. The dental instrument of claim 2, wherein said spring includes a first end and a second end, the first end of the spring being positioned against a shoulder of said collet, the second end of the spring applying force to a back end of the grip portion to urge the dental tip entrance end of the grip portion axially toward the dental tip retaining portion of the spring fingers of said collet.

4. The dental instrument of claim 3, wherein the outer surface of the dental tip retaining portion of the spring fingers tapers radially inward.

5. The dental instrument of claim 1, wherein the dental tip retaining portion of the spring fingers includes an outer surface engageable with an internal surface of the bore of said collar.

6. The dental instrument of claim 5, wherein the spring fingers are urged radially inward by engagement of the outer surface of the dental tip retaining portion of the spring fingers and an internal surface defining the bore of said collar when the first surface of the handle center is in the first axial position relative to the grip portion.

7. The dental instrument of claim 1, wherein the handle center of said handle is molded around said center rod.

8. The dental instrument of claim 1, wherein the multiple inclined plane surfaces of the first surface of the handle center includes a first inclined surface and the multiple inclined plane surfaces of the second surface of the grip portion includes a second inclined surface, wherein the translation along the axis of the grip portion relative to the handle center between the first axial position and the second axial position results from contact of the first inclined surface of the handle center with the second inclined surface of the grip portion during rotation of the grip portion relative to the handle center.

9. The dental instrument of claim 1, wherein the second end of said dental tip includes a flat surface extending axially along the axis, wherein the dental tip retaining portion of the spring fingers receives the flat surface of the second end of said dental tip.

10. The dental instrument of claim 1, wherein said collar is press fit into the grip portion of said handle.

11. The dental instrument of claim 1, wherein the grip portion is rotatable three hundred and sixty degrees relative to the handle center.

12. The dental instrument of claim 1, wherein said dental instrument can be sterilized.

13. The dental instrument of claim 1, wherein the first end of said dental tip is curved.

14. The dental instrument of claim 1, wherein the first surface of the handle center is recessed from an end of the handle center.

15. The dental instrument of claim 1, wherein said collet is press fit onto said center rod.

16. A dental instrument, said dental instrument comprising:
   a first dental tip, said first dental tip including a first end and a second end;
   a second dental tip, said second dental tip including a first end and a second end;
   a handle, said handle including a handle center, a first grip portion and a second grip portion, said handle including an axis and an elongated opening extending along said axis though the handle center, the first grip portion and the second grip portion, the handle center including a first surface proximate a first end and a second surface proximate a second end, wherein the first surface of the handle center includes multiple inclined plane surfaces, the first grip portion including a dental tip entrance end for receiving the first dental tip and a second surface in engagement with the first surface of the handle center, wherein the second surface of the first grip portion includes multiple inclined plane surfaces, the second surface of the first grip portion being rotatable about the axis relative to the first surface of the handle center, wherein rotation of the second surface of the first grip portion relative to the first surface of the handle center causes translation along the axis of the first grip portion relative to the handle center between a first axial position and a second axial position;

the second grip portion including a dental tip entrance end for receiving the second dental tip and a second surface in engagement with the second surface of the handle center, the second surface of the second grip portion being rotatable about the axis relative to the second surface of the handle center, wherein rotation of the second surface of the first grip portion relative to the second surface of the handle center causes translation along the axis of the second grip portion relative to the handle center between a third axial position and a fourth axial position;

a first collar, said first collar disposed within the elongated opening proximate the dental tip entrance end of the first grip portion, said first collar including a bore extending along the axis between a first opening proximate the dental tip entrance end of the first grip portion and a second opening;

a first collet, said first collet including a body portion and spring fingers extending from the body portion, the spring fingers including a dental tip retaining portion configured to receive the second end of the first dental tip, the spring fingers being urged radially inward by said first collar towards the axis to secure the second end of said first dental tip when the first grip portion is in the first axial position relative to the first surface of the handle center, the second end of said first dental tip being removable from the dental tip retaining portion of the spring fingers of said first collet when the first grip portion is in the second axial position relative to the first surface of the handle center;

a second collar, said second collar disposed within the elongated opening proximate the dental tip entrance end of the second grip portion, said second collar including a bore extending along the axis between a first opening proximate the dental tip entrance end of the second grip portion and a second opening;

a second collet, said second collet including a body portion and spring fingers extending from the body portion, the spring fingers including a dental tip retaining portion configured to receive the second end of the second dental tip, the spring fingers being urged radially inward by said second collar towards the axis to secure the second end of said second dental tip when the second grip portion is in the third axial position relative to the second surface of the handle center, the second end of said second dental tip being removable from the dental tip retaining portion of the spring fingers of said second collet when the second grip portion is in the fourth axial position relative to the second surface of the handle center; and a center rod, said center rod extending along the axis, a portion of said center rod being retained by the handle center, said center rod including a first end affixed to the body portion of said first collet and a second end affixed to the body portion of said second collet.

17. The dental instrument of claim 16, further comprising:
a first spring housed within the first grip portion, said first spring being operative on the first grip portion for urging the dental tip entrance end of the first grip portion axially toward the dental tip retaining portion of the spring fingers of said first collet; and
a second spring housed within the second grip portion, said second spring operative on the second grip portion for urging the dental tip entrance end of the second grip portion axially toward the dental tip retaining portion of the spring fingers of said second collet.

18. A dental instrument, said dental instrument comprising:
a dental tip, said dental tip including a first end and a second end;
a handle, said handle including a handle center and a grip portion, said handle including an axis and an elongated opening extending along the axis though the handle center and the grip portion, the handle center including a first surface, wherein the first surface of the handle center includes multiple inclined plane surfaces, the grip portion including a dental tip entrance end and a second surface, wherein the second surface of the grip portion includes multiple inclined plane surfaces, the second surface of the grip portion being rotatable about the axis relative to the first surface of the handle center, wherein rotation of the second surface of the grip portion relative to the first surface of the handle center causes translation along the axis of the grip portion relative to the handle center between a first axial position and a second axial position;
a collar, said collar disposed within the elongated opening proximate the dental tip entrance end of the grip portion; and
a collet, said collet including an end and a dental tip retaining portion opposite the end, the dental tip retaining portion configured to receive the second end of the dental tip, the dental tip retaining portion of said collet being urged radially inward by said collar towards the axis to secure the second end of said dental tip when the grip portion is in the first axial position relative to the handle center, the second end of said dental tip being removable from the dental tip retaining portion when the grip portion is in the second axial position relative to the handle center, wherein the end of said collet is affixed to the handle center.

19. The dental instrument of claim 18; wherein said handle center includes an outer housing and a first rod having a first end and a second end, the first rod extending along the axis, the first end of the first rod affixed to the outer housing of the handle center, the second end of the first rod affixed to the end of said first collet.

20. The dental instrument of claim 19, further comprising:
a second dental tip, said dental tip including a first end and a second end; a second grip portion including a second dental tip entrance end for receiving a second dental tip and a first surface in engagement with a second surface of the handle center, the first surface of the second grip portion being rotatable about the axis relative to the second surface of the handle center, wherein rotation of the first surface of the second grip portion relative to the second surface of the handle center causes axial movement of the second grip portion relative to the handle center between a third axial position and a fourth axial position;
a second collar, said second collar disposed within the elongated opening proximate the second dental tip entrance end of the second grip portion; and
a second collet, said second collet including an end and a dental tip retaining portion configured to receive the second end of the second dental tip, the dental tip retaining portion of said second collet being urged radially inward by said second collar towards the axis to secure the second end of said second dental tip when the second grip portion is in the third axial position relative to the handle center, the second end of said second dental tip being removable from the dental tip retaining portion of said second collet when the second grip portion is in the fourth axial position relative to the handle center, said center rod including a second end affixed to said second collet, wherein said handle center includes a second rod having a first end and a second end, the second rod extending along the axis, the first end of the second rod is affixed to the outer housing of the handle center, the second end of the second rod affixed to the end of said second collet.

21. The dental instrument of claim 20, further comprising:
a first spring housed within the first grip portion, said first spring pushingly engages the first grip portion for urging the dental tip entrance end of the first grip portion axially toward the dental tip retaining portion of the spring fingers of said first collet; and
a second spring housed within the second grip portion, said second spring pushingly engages the second grip portion for urging the dental tip entrance end of the second grip portion axially toward the dental tip retaining portion of the spring fingers of said second collet.

22. The dental instrument of claim 20, wherein the first end of the first rod and the first end of the second rod are connected.

* * * * *